United States Patent [19]

Edwards

[11] Patent Number: 5,529,495
[45] Date of Patent: Jun. 25, 1996

[54] RIGHT ANGLE DENTAL HAND PIECE WITH SPRING DRIVE

[76] Inventor: Donald L. Edwards, 10417 - 24th Ave. SE., Monroe, Wash. 98272

[21] Appl. No.: 465,825

[22] Filed: Jun. 6, 1995

[51] Int. Cl.[6] ..................................................... A61C 1/18
[52] U.S. Cl. ............................................. 433/112; 433/125
[58] Field of Search ..................................... 433/112, 125

[56] References Cited

U.S. PATENT DOCUMENTS

| | | |
|---|---|---|
| 472,683 | 4/1892 | Pedersen ................................. 453/112 |
| 691,753 | 1/1902 | Dean ................................. 433/112 X |
| 745,722 | 12/1903 | Freeman . |
| 941,612 | 11/1909 | Browne . |
| 2,105,330 | 1/1938 | Pagenkopt . |
| 3,472,045 | 10/1969 | Nelsen et al. . |
| 3,740,853 | 6/1973 | Bradler ................................. 433/112 |
| 3,757,419 | 9/1973 | Hopkins . |
| 3,906,636 | 9/1975 | Rainey et al. . |
| 4,021,918 | 5/1977 | Bailey . |
| 4,060,870 | 12/1977 | Cannarella ........................... 433/112 X |
| 5,169,312 | 12/1992 | Berlin ................................. 433/112 X |

FOREIGN PATENT DOCUMENTS 873251  7/1942  France ................................. 433/112

Primary Examiner—Nicholas D. Lucchesi
Attorney, Agent, or Firm—Graybeal Jackson Haley and Johnson

[57] ABSTRACT

An angle drive dental hand piece or prophy with a drive train including an essentially cylindrical spindle frictionally engaged by the turns of a spiral spring. The driving end of the spring which in turn rotates a tool holder carrying a dental tool such as a rubber scrubber. The drive spring is bent at an angle such as a right angle while being rotated and is of a diameter in relation to the housing bore through which it passes so that there is no engagement or consequent friction from any contact of the spring with the bore housing. Overload on the tool causes slippage between the spring and the spindle on which it is wound so that damage to the drive train components from overload is avoided.

4 Claims, 1 Drawing Sheet

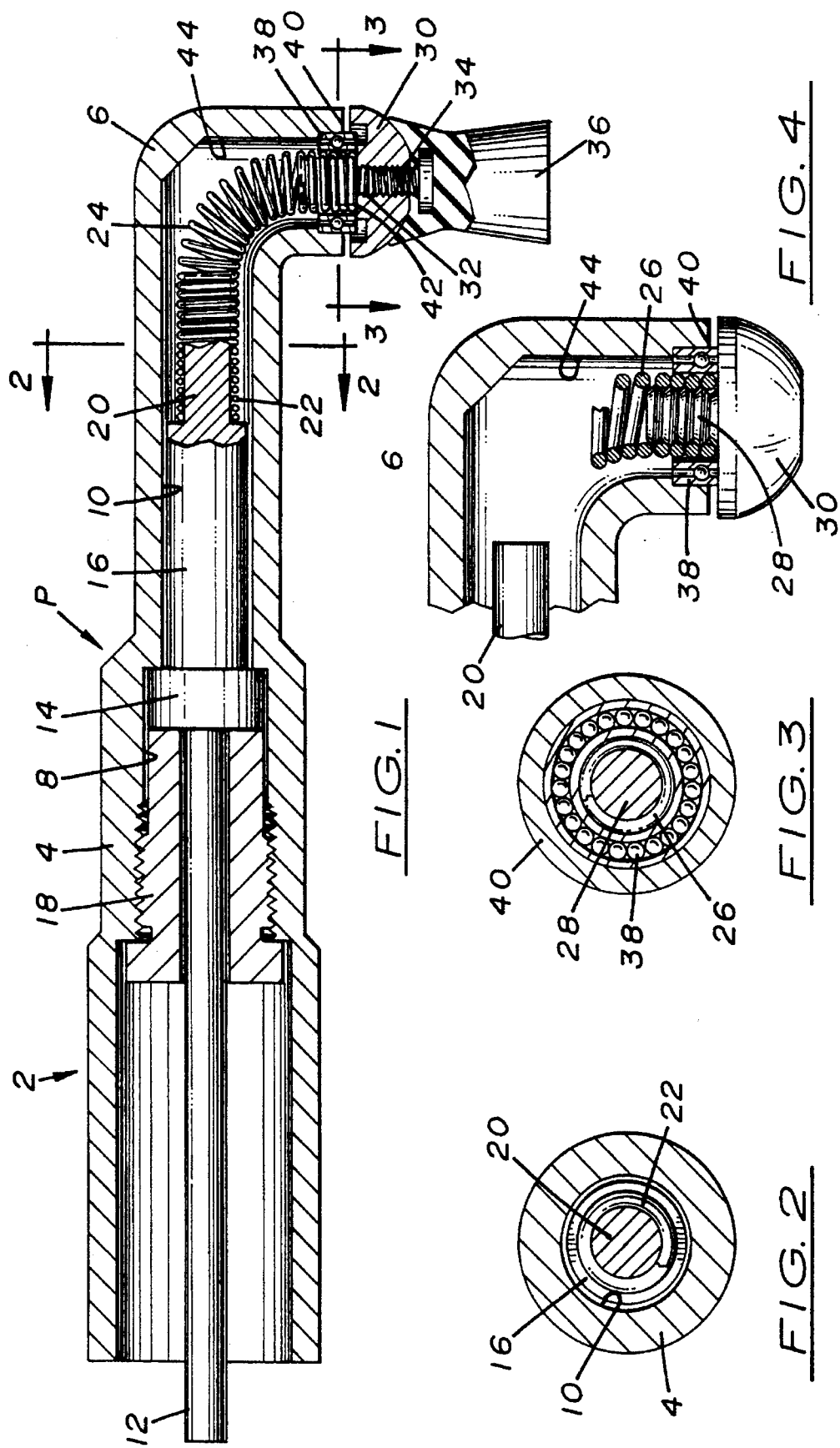

RIGHT ANGLE DENTAL HAND PIECE WITH SPRING DRIVE

BACKGROUND OF THE INVENTION

1. Field of the Invention

This invention relates to dental tools and more particularly to right angle dental hand pieces, also known as prophys, which are hand held in use while being power driven from a separate rotary power source, conventional per se.

2. Description of the Prior Art

Hand held dental tools which are arranged at an angle, usually at a right angle, with respect to a handle portion through which rotary power is delivered to drive the tool are most commonly gear driven with meshed gears in right angle or other angular arrangement at the head of the tool body. In use of such intermeshed gear drives, the driven tool, such as a soft rubber scrubber in common use for the cleaning of teeth, can become overheated, causing patient pain, and there is risk of the gear teeth breaking if the tool becomes jammed or restricted in its rotation with the result that too much torque is applied to the gear teeth.

Also known is a hand held dental tool drive of a more or less right angle configuration which involves a coiled spring in the drive train, such as disclosed in Freeman U.S. Pat. No. 745,722. However, in the Freeman tool the coiled spring in the drive train from the drive shaft to the tool is keyed at one end to the drive sprindle and also keyed at the other end to the tool so there is no relief in the drive train from over-torquing and overheating at the tool in the event of excessive pressure at the tool or drag on the tool.

Also known in right angle drive hand held dental tools is an arrangement Where the right angle drive is applied through a flexible cable, as in Hopkins U.S. Pat. No. 3,757,419. However, in the Hopkins drive arrangement, the flexible drive cable if fixedly attached to the motor drive shaft at its driven end and fixedly attached to the tool connector element at its driving end so that it has a like limitation as to a lack of relief from over-torquing in a manner similar to that characteristic of the Freeman drive arrangement.

Also known is a dental tool angle drive arrangement as in Nelsen et al U.S. Pat. No. 3,472,045, in which the interconnection between a drive shaft and the dental tool is by means of an elastomeric shaft with rigid interconnection to a drive shaft at one end and to a tool coupler at the other end. In the forms of elastomeric drive shafts as disclosed and discussed in said Nelsen et al U.S. patent, the drive shafts are described as being in frictional engagement with the defining surface of the housing bore in which they rotate. Such arrangements inherently generate friction and heat in the hand piece during use, in addition to being subject to unrelieved torque load in the event of excess pressure being applied to the tool.

Known as well is use in a dental hand piece of a spiral spring as a tool holder, such as in the hand piece disclosed in Bailey U.S. Pat. No. 4,021,918. However, in the Bailey arrangement, while the dental instrument such as a drill is held in the hand piece by tightening of the coils of a spring around the shank of the instrument, the drive train down to the tool holder itself involves conventional right angle related toothed gears or a conventional air driven turbine drive.

SUMMARY OF THE INVENTION

The present invention provides a drive train arrangement for a right angle hand held dental tool or prophy which incorporates automatic protection against overload on the tool and consequent over-torquing of the drive train, which is characterized by low order friction and heat generation during use, which is economical and simple to manufacture, which do not require any lubrication during use, and which when used for dental tooth cleaning, inherently avoids any likelihood of patient discomfort from tooth overheating while being cleaned by a conventional soft rubber scrubber. It is also a feature of the invention to provide a hand held dental tool with automatic protection against overload which has a long useful life before needing repair or replacement, which are reusable, and in which components parts of the drive train are readily replaceable.

These and other objects, features and advantages of the invention will be apparent to those skilled in the art in view of the specific embodiment thereof illustrated in the accompanying drawing and described below.

BRIEF DESCRIPTION OF THE DRAWING

FIG. 1 is a side elevational view of a right angle drive dental hand piece with a polishing cup shown as the dental tool.

FIG. 2 is a lateral cross-sectional view through the drive spindle and associated parts of the hand piece shown in FIG. 1, taken substantially along line 2—2 thereof.

FIG. 3 is a lateral cross-sectional view through the bearing adjacent the tool holder of the hand piece shown in FIG. 1, taken substantially along line 3—3 thereof.

FIG. 4 is a detail view in elevation and cross-section of a portion of the head end of the hand tool shown in FIG. 1 with much of the drive spring broken away to show further detail with respect to the drive spindle and the interengagement of the drive spring with the tool holder shank and associated ball bearing.

DESCRIPTION OF THE PREFERRED EMBODIMENT

The dental hand piece or prophy P shown in FIG. 1 comprises a housing or body 2 with a tubular shank 4 and a head end 6, said shank 4 in turn comprising an inner bore 8 and an outer bore 10. Arranged axially of the housing 2 and shank 4 is a drive shaft 12 comprising a flange 14 and spindle 16, the shaft 12, flange 14 and spindle 16 being removably retained in place for rotation within the housing 2 and shank 4 by spindle nut 18 which is in threaded engagement with matching threads on the inner bore 8 of shank 4. As will be understood, the components of the hand piece P described above are structurally compatible with what is known as a Doriot type hand piece for connection of the hand piece with a coupling or the like that is in turn connected with a source of rotary power as is common in conventional dental equipment.

Drive shaft 12, flange 14, and spindle portions 16 and 20 are suitably fabricated in one piece of aluminum alloy which is subject to hard anodized surface treatment to have a Rockwell hardness of 60–65 and provided with a heat treated Teflon coating, e.g. Lubricote.

Housing 2 is suitably formed of cast aluminum alloy with machined inner surfaces.

In a manner characteristic of the present invention the spindle 16 includes a smaller diameter, concentric, cylindrical, smooth surfaced outer spindle 20 on which is snuggly fitted the driven end 22 of a spiral drive spring generally indicated at 24, the driving end 26 of which is in threaded engagement with the threaded shank 28 of a generally hemispherical tool holder 30, which is conventional per se and has an internally threaded bore 32 into which the threaded connector 34 of a conventional rubber scrubber cup 36 is threaded to mount the cup 36 on the tool holder 30. As shown in FIGS. 1 and 4, a ball bearing 38 journals the driving end 26 of the spring 24 and the tool holder 30 engaged thereby, with the outer race of the bearing 38 spring pressed into the open bore 40 of the hand piece head end 6 and the end turn of the spring end 26 lodged against the inner race of the bearing 38 and against the inner face 42 (FIG. 1) of the tool holder 30.

FIG. 4 shows the smaller diameter portion 20 of the spindle 16 in elevation, and without the driven end 22 of the spring 24 thereon, to more clearly illustrate the smooth surface thereof which, as earlier indicated, is essentially cylindrical in configuration, also noting its lateral cross section in this respect as shown in FIG. 2.

As shown in FIG. 1, it is an important feature of the hand piece that there is no contact between the drive spring 24 and the bore 10 or the wall 44 of the head end 6 of the hand piece. By this arrangement, there is no friction or consequent heat generation and drag as a result of contact of the drive spring with the bore 10 or wall 44. As a result, the drive train of the hand piece, including the drive spring 24, runs relatively cool and is long lasting even considering that it is common in use of such hand pieces to operate them for substantial periods at speeds of 1200–1500 rpm and higher.

The inner diameter of the driven end 22 of spring 24 is selected to snuggly fit onto the spindle end 20. Such spring is commonly a right turn spring for use with a drive spindle which is normally driven in a clockwise manner. In such an arrangement, when the driven dental tool is under load, there is sufficient friction grip of the turns of the spring on the spindle end 20 to maintain rotation of the drive spring 24 and the tool, e.g. the cup 36. However, should an overload condition develop, such as by the user exerting too much pressure on the tool, the spindle end 20 slips within the spring end 22 and in effect decouples the drive and interrupts rotation of the tool until the overload is removed. This manner of driving a dental hand piece tool does not involve any likelihood of any undue heating or breakage of drive train components because the spindle end 20 and spring end 22 are both metallic. At least as important is the consideration that with such overload responsive decoupling of the hand piece tool drive, the dental patient on which the tool is being used is much less likely to be subjected to rotating tool over-pressure and consequent pain or at least discomfort.

Driving of the spindle end 20 and consequently the spring 24 in a reverse, e.g. counterclockwise, manner is customary practice in this type of hand piece to remove a given tool from the tool holder, i.e. by unthreading connector 34 from the threaded bore 32 of the tool holder 30 and this can be done readily without undue overload.

As an example of a suitable drive spring for use in practice of the present invention in the hand piece illustrated and discussed above, a given coil spring for the purpose can be fabricated from 17–7 stainless steel, heat treated, with the spring having an O.D. of 0.125, a coil diameter of 0.015, and a length of 1.25 inch. With respect to the bearing 38, it is considered advantageous to provide such with Teflon particles containing Super Lube grease, obtainable from Permatex Industrial of Newington, Conn. This grease is especially suitable for the purpose because it withstands high temperatures (350° F. and above) and is water resistant which renders hand pieces according to the invention autoclavable without disassembly.

From the foregoing, other modifications, variations and adaptations of the invention will occur to those skilled in the art to which the invention is addressed, within the scope of the following claims.

What is claimed is:

1. A dental hand piece comprising:

a main body including a housing with a driven tool holder arranged on one end of said housing, said tool holder being arranged to be rotated about an axis substantially at an angle relative to the longitudinal dimension of said main body;

a cylindrical, smooth surfaced drive spindle arranged in said housing and rotated about an axis extending in said housing along the longitudinal dimension of the main body;

a coil spring coupling arranged with one end thereof spiralled around, extending coaxially of, and driven by said spindle and with the other end of said coil spring coupling connected to said driven tool holder, said coil spring coupling being arranged within and spaced from said housing and in contact with only said spindle and said driven tool holder, with torque transfer from said spindle to said coil spring coupling being solely through frictional engagement therebetween, and with said coil spring coupling adapted to slip on said spindle in the event of torque overload occurring at the driven tool holder.

2. A dental handpiece according to claim 1, wherein said dental hand piece is a prophy and said driven tool is an elastomeric tooth scrubber.

3. A dental handpiece according to claim 2, wherein the axis of rotation of said tool holder is at a right angle relative to the longitudinal dimension of said main body.

4. A dental handpiece according to claim 1, wherein the axis of rotation of said tool holder is at a right angle relative to the longitudinal dimension of said main body.

* * * * *